(12) United States Patent
Yoshida et al.

(10) Patent No.: US 9,215,887 B2
(45) Date of Patent: Dec. 22, 2015

(54) METHOD FOR INHIBITING COLORING OF A SYRUPY SWEETENER COMPRISING A NON-REDUCING OLIGOSACCHARIDE HAVING A BETA-FRUCTOFRANOSIDIC LINKAGE AND A REDUCING SACCHARIDE, AND USE THEREOF

(75) Inventors: Kenshi Yoshida, Okayama (JP); Ikuo Sawatani, Okayama (JP); Hiroto Chaen, Okayama (JP); Shigeharu Fukuda, Okayama (JP); Toshio Miyake, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 646 days.

(21) Appl. No.: 12/990,729

(22) PCT Filed: Apr. 27, 2009

(86) PCT No.: PCT/JP2009/058254
§ 371 (c)(1),
(2), (4) Date: Nov. 2, 2010

(87) PCT Pub. No.: WO2009/133835
PCT Pub. Date: Nov. 5, 2009

(65) Prior Publication Data
US 2011/0045137 A1    Feb. 24, 2011

(30) Foreign Application Priority Data

May 2, 2008    (JP) ................. 2008-120261

(51) Int. Cl.
| | |
|---|---|
| A23L 1/09 | (2006.01) |
| A23L 1/236 | (2006.01) |
| A23C 9/13 | (2006.01) |
| A23C 9/154 | (2006.01) |
| A23C 11/04 | (2006.01) |
| A23K 1/16 | (2006.01) |
| A23L 1/03 | (2006.01) |
| A23L 1/06 | (2006.01) |
| A23L 1/272 | (2006.01) |
| A23L 2/60 | (2006.01) |
| C12P 19/00 | (2006.01) |
| C12P 19/18 | (2006.01) |
| A23L 1/30 | (2006.01) |

(52) U.S. Cl.
CPC ............. *A23L 1/2363* (2013.01); *A23C 9/1307* (2013.01); *A23C 9/1544* (2013.01); *A23C 11/04* (2013.01); *A23K 1/1643* (2013.01); *A23K 1/1646* (2013.01); *A23L 1/0315* (2013.01); *A23L 1/06* (2013.01); *A23L 1/09* (2013.01); *A23L 1/272* (2013.01); *A23L 2/60* (2013.01); *C12P 19/00* (2013.01); *C12P 19/18* (2013.01); *C12Y 204/01019* (2013.01); *C12Y 302/01026* (2013.01); *A23V 2002/00* (2013.01)

(58) Field of Classification Search
CPC .................... A23V 2002/00; A23V 2200/044
USPC .......................................................... 426/64
See application file for complete search history.

(56) References Cited

U.S. PATENT DOCUMENTS

| | | | |
|---|---|---|---|
| 3,894,146 A | | 7/1975 | Tsuyama |
| 5,032,509 A | * | 7/1991 | Matsumoto et al. ............ 435/42 |
| 5,455,235 A | * | 10/1995 | Takaichi et al. ................. 514/54 |
| 5,523,099 A | | 6/1996 | Aga et al. |
| 5,753,469 A | * | 5/1998 | Nakada et al. .................. 435/99 |
| 5,780,620 A | | 7/1998 | Mandai et al. |
| 7,029,717 B1 | | 4/2006 | Ojima et al. |
| 2008/0027027 A1 | | 1/2008 | Okabe et al. |

FOREIGN PATENT DOCUMENTS

| | | |
|---|---|---|
| EP | 0780470 A2 | 6/1997 |
| EP | 1219630 A1 | 7/2002 |
| EP | 1746164 A1 | 1/2007 |
| JP | S58167516 A | 10/1983 |
| JP | 7-163386 A | 6/1995 |
| JP | 8-127587 A | 5/1996 |
| JP | 9-224665 A | 9/1997 |
| JP | 10-23875 A | 1/1998 |
| JP | 11-124390 A | 5/1999 |
| KR | 20070010062 A | 1/2007 |
| KR | 100751865 B1 | 8/2007 |
| WO | WO 0062628 A1 | 10/2000 |

OTHER PUBLICATIONS

Gryuner V S et al "The effect of Stabilizing salts on the properties of sugar solutions during heating.(translated)", Database FSTA [online] International Food Information Service (IFIS), Frankfurt-Main DE XPO02737835, 47 (2) 40-43 (1973) abstract.

* cited by examiner

*Primary Examiner* — D. Lawrence Tarazano
*Assistant Examiner* — Philip Dubois
(74) *Attorney, Agent, or Firm* — Browdy and Neimark, P.L.L.C.

(57) ABSTRACT

The objects of the present invention are to provide a method for inhibiting the coloration of a syrupy sweetener, comprising a reducing saccharide together with a non-reducing oligosaccharide having a β-fructofuranosidic linkage, without deteriorating the taste inherent to the syrupy sweetener; and to provide a syrupy sweetener, comprising a reducing saccharide together with a non-reducing oligosaccharide having a β-fructofuranosidic linkage, which is stabilized by the method. The present invention attains the above objects by providing a method for inhibiting the coloring of a syrupy sweetener, comprising a reducing saccharide together with a non-reducing oligosaccharide having a β-fructofuranosidic linkage, which comprises a step of incorporating a lactate into the syrupy sweetener, and by providing a syrupy sweetener, comprising a reducing saccharide together with a non-reducing oligosaccharide having a β-fructofuranosidic linkage, which is stabilized by the method.

2 Claims, No Drawings

METHOD FOR INHIBITING COLORING OF A SYRUPY SWEETENER COMPRISING A NON-REDUCING OLIGOSACCHARIDE HAVING A BETA-FRUCTOFRANOSIDIC LINKAGE AND A REDUCING SACCHARIDE, AND USE THEREOF

TECHNICAL FIELD

The present invention relates to a method for inhibiting the coloration of a syrupy sweetener containing a reducing saccharide together with a non-reducing oligosaccharide having a β-fructofuranosidic linkage, more particularly, to a method for inhibiting the coloration of a syrupy sweetener containing a reducing saccharide together with a non-reducing oligosaccharide having a β-fructofuranosidic linkage, characterized in that it contains a step of incorporating a lactate into the syrupy sweetener, and use thereof.

BACKGROUND ART

Recently, the functional properties of oligosaccharides have been revealed and practically used respectively in various use of foods, pharmaceuticals, etc. Among these oligosaccharides, non-reducing oligosaccharides having a β-fructofuranosidic linkage have, as a characteristic property, a preferable feature relatively close to sugar (or sucrose) in term of sweetness or the like; and they are used in the following as main ingredients that exert various functions: For example, lactosucrose, where galactose is bound to the glucose residue of sucrose via the β-1,4 linkage, which has substantially-hard digestibility, bifid-bacterium-growth-promoting property, substantially-free cariogenicity, and moisture-retaining ability; glycosylsucrose, where glucose or maltooligosaccharide is bound to the glucose residue of sucrose, which has crystallization-preventing action on sugar, moisture-retaining ability, and substantially-free cariogenicity; and fructooligosaccharide, where fructose or fructooligosaccharide is bound to the fructose residue of sucrose via the β-1,2 linkage, which is easily assimilated by bifid bacteria and capable of improving intestinal flora have been used in food products, cosmetics, and pharmaceuticals for the purpose of, for example, improving physical properties, improving taste, inhibiting cariogenicity, improving bacterial flora, and controlling immunity.

As disclosed in, for example, Japanese Patent Kokai No. 224,665/97, lactosucrose is prepared by allowing a β-fructofuranosidase derived from a microorganism to act on a solution containing sucrose and lactose through saccharide-transferring reaction catalyzed by the β-fructofuranosidase. As disclosed in, for example, Japanese Patent Kokoku No. 17,660/78, glycosylsucrose is prepared by allowing a cyclomaltodextrin glucanotransferase derived from a microorganism to act on a solution containing sucrose and partial starch hydrolyzate. As disclosed in, for example, Japanese Patent Kokai No. 201,980/83, fructooligosaccharide is prepared by allowing a β-fructofuranosidase derived from a microorganism to act on sucrose.

As disclosed in the above Japanese Patent Kokai No. 224,665/97, Japanese Patent Kokoku No. 017,660/78, and Japanese Patent Kokai No. 201,980/83, a non-reducing oligosaccharide having a β-fructofuranosidic linkage is prepared by allowing a saccharide-transferring enzyme to act on an oligosaccharide containing sucrose through a saccharide-transferring reaction from an oligosaccharide to another oligosaccharide. In practicing the reaction, the objective non-reducing oligosaccharide, which consists of a tri-saccharide or higher having a β-fructofuranosidic linkage, is formed along with, for example, one or more reducing saccharides selected from glucose, fructose, galactose, maltose, lactose, and maltotriose, which are inevitably formed as by-products.

The objective non-reducing oligosaccharide has been commercialized in the market as a syrupy sweetener product after the non-reducing oligosaccharide coexisted with the above by-products is subjected to purification steps such as decoloration with an activated charcoal and desalting with ion-exchange resins in H- and OH-form. Such a syrupy sweetener, which contains a reducing saccharide together with a non-reducing oligosaccharide having a β-fructofuranosidic linkage, has been revealed to have a defect of being easily colored through deterioration and browning during storage at ambient temperature. To avoid such a defect as much as possible, a cold storage is needed, however, such a cooling increases both the viscosity of the syrupy sweetener and the transportation/storage cost as the drawbacks.

As a method for stably keeping lactosucrose in a lactosucrose-containing-composition for inhibiting abdominal abnormality, for example, Japanese Patent Kokai No. 265,390/98 proposes to adjust the pH to a level of 6.6 to 7.5 by using an organic acid or the like, or a salt thereof as a pH buffer. The method keeps lactosucrose stably, however, it easily causes coloration and loses the product value of a syrupy sweetener containing a reducing saccharide together with a non-reducing oligosaccharide having a β-fructofuranosidic linkage when applied thereunto. Further, it was also revealed that the preferable sweetness inherent to the syrupy sweetener is deteriorated to lose its product value as a sweetener by the unsatisfactory taste such as salty and astringent taste inherent to the organic acid or the like and the salt thereof used as a pH buffer.

DISCLOSURE OF INVENTION

Object of the Invention

In view of the foregoing, the present invention has the first object to provide a method for inhibiting the coloration of a syrupy sweetener containing a reducing saccharide together with a non-reducing oligosaccharide having a β-fructofuranosidic linkage, particularly, to a method for inhibiting the coloration of the syrupy sweetener without losing its inherent preferable taste; and has the second object to provide a syrupy sweetener, containing a reducing saccharide together with a non-reducing oligosaccharide having a β-fructofuranosidic linkage, whose coloration is inhibited by the above method.

Means to Attain the Object

To overcome the above objects, the present inventors have diligently screened and studied the use of organic acid salts. As a result, they unexpectedly found that the coloration of a syrupy sweetener, containing a reducing saccharide together with a non-reducing oligosaccharide having a β-fructofuranosidic linkage, is inhibited at ambient temperature by incorporating a lactate at a concentration of 0.2 to 2.0 mM, preferably, 0.2 to 1.5 mM, into the syrupy sweetener. They also found that, when a lactate is incorporated into the syrupy sweetener at a concentration within the above range, the content reduction of the non-reducing oligosaccharide is inhibited and the syrupy sweetener is stably stored at ambient temperature. Further, they found that the preferable taste inherent to the syrupy sweetener is not deteriorated, even when a lactate is incorporated into the syrupy sweetener within the above range. Thus, they accomplished this invention.

The present invention attains the above objects by providing a method for inhibiting coloration of a syrupy sweetener containing a reducing saccharide together with a non-reducing oligosaccharide having a β-fructofuranosidic linkage, characterized in that it contains a step of incorporating a lactate at a concentration of 0.2 to 2.0 mM, preferably, 0.2 to 1.5 mM; and providing a syrupy sweetener which contains a reducing saccharide together with a non-reducing oligosaccharide having a β-fructofuranosidic linkage and which has been stabilized by the method. Also, the present invention attains the above objects by establishing a coloration inhibitory agent for a syrupy sweetener, which contains a lactate as an effective ingredient; and by designing the use thereof.

Effect of the Invention

According to the method for inhibiting coloration of a syrupy sweetener containing a reducing saccharide together with a non-reducing oligosaccharide having a β-fructofuranosidase linkage of the present invention, there is produced a stable syrupy sweetener containing a reducing saccharide together with a non-reducing oligosaccharide having a β-fructofuranosidase linkage, particularly, a syrupy sweetener which contains a reducing saccharide together with a non-reducing oligosaccharide having a β-fructofuranosidase linkage and which is stably stored at ambient temperature for a relatively long period of time, where the coloration of syrupy sweetener is inhibited without deteriorating the taste inherent to the syrupy sweetener and also the content reduction of the non-reducing oligosaccharide having a β-fructofuranosidic linkage, as the main ingredient of the sweetener, is inhibited.

BEST MODE FOR CARRYING OUT THE INVENTION

The lactates used in the present invention include salts composed of lactic acid ion and other cation that are ionically bonded together, wherein the cation as a counter ion is not specifically restricted as long as it exerts coloration inhibitory effect on the syrupy sweetener of the present invention. Preferable examples of the lactates used in the present invention include those which are approved as food additives; sodium lactate, calcium lactate, and ferrous lactate, wherein the sodium lactate or calcium lactate is suitable in terms of its color and taste.

The term "a non-reducing oligosaccharide having a β-fructofuranosidic linkage" as referred to as in the present invention means a non-reducing oligosaccharide, which is composed of di-saccharide or higher having intramolecularly the structure of a fructose residue linked via a β-fructofuranosidic linkage; sucrose as a disaccharide, and other tri-saccharide or higher such as lactosucrose (or galactosylsucrose), glycosylsucrose including glucosylsucrose (or erlose), and fructooligosaccharides including fructosylsucrose (or ketose) and isoketose.

The term "a method for producing a syrupy sweetener containing a reducing saccharide together with a non-reducing oligosaccharide having a β-fructofuranosidic linkage" as referred to as in the present invention is not specifically restricted, and preferable ones are as follows: A production method containing the steps of allowing a saccharide-transferring enzyme, for example, β-fructofuranosidase, cyclomaltodextrin glucanotransferase, or the like, to act on an aqueous oligosaccharide solution containing sucrose with or without lactose, or containing sucrose and dextrin to form a reducing saccharide together with a non-reducing oligosaccharide having a β-fructofuranosidic linkage; purifying the resulting mixture through decoloration with an activated charcoal and desalting with an ion-exchange resin; and incorporating a lactate into the resulting purified-product. The term "a syrupy sweetener containing a reducing saccharide together with a non-reducing oligosaccharide having a β-fructofuranosidic linkage" as referred to as in the present invention means those which usually have a solid concentration of 30 w/w % to 80 w/w %, preferably, 50 w/w % to 75 w/w %; contain an oligosaccharide(s) at a concentration of at least 10 w/w %, preferably, 20 w/w % to 80 w/w %, and more preferably, 30 w/w % to 70 w/w %, on a dry solid basis (d.s.b.); and contain a reducing saccharide(s) such as glucose, fructose, lactose, and maltooligosaccharides at a concentration of at least 1 w/w %, preferably, at least 10 w/w %, d.s.b.

The term "coloration inhibition of a syrupy sweetener containing a reducing saccharide together with a non-reducing oligosaccharide having a β-fructofuranosidic linkage" as referred to as in the present invention means the inhibition of coloration of the syrupy sweetener that is inducible when stored at ambient temperature.

When the lactate as referred to as in the present invention is incorporated into a syrupy sweetener containing a reducing saccharide together with a non-reducing oligosaccharide having a β-fructofuranosidic linkage, the step for incorporating the lactate can be made before completion of the production step of the syrupy sweetener of the present invention, and preferably be made after the purification step of decoloring and desalting. Examples of such include a method of incorporating a lactate in the form of a powder or liquid and/or an aqueous solution thereof by an appropriate method of mixing, kneading, dissolving, injecting, etc.

The concentration of a lactate to be incorporated into a syrupy sweetener, containing a reducing saccharide together with a non-reducing oligosaccharide having a β-fructofuranosidic linkage, should not specifically be restricted as long as the syrupy sweetener can be stably stored and the taste inherent to the syrupy sweetener is not deteriorated. The preferable concentrations usable in the present invention are 0.2 to 2.0 mM, more preferably, 0.2 to 1.5 mM as a lactate(s). The desired stabilization effect is not sufficiently exerted at concentrations of less than 0.1 mM of a lactate(s); while, when the concentration exceeds 2.0 mM, it may cause unfavorable taste such as salty and astringent taste when ingested orally. Particularly, in the case of using calcium lactate as a lactate, sediments may be formed. The syrupy sweetener containing a reducing saccharide together with a non-reducing oligosaccharide having a β-fructofuranosidic linkage is usually set to a pH of 4.0 to 6.4, preferably, 4.2 to 5.8. When the pH of the syrupy sweetener containing a reducing saccharide together with a non-reducing oligosaccharide having a β-fructofuranosidic linkage is below 4.0 or over 6.4, there may be induced problems of that the coloration inhibitory effect may be lowered or the taste inherent to the syrupy sweetener may be deteriorated.

By using the method for inhibiting the coloration of a syrupy sweetener containing a reducing saccharide together with a non-reducing oligosaccharide having a β-fructofuranosidic linkage, the coloration of the syrupy sweetener can be inhibited without deteriorating the taste inherent to the sweetener and also the content reduction of the non-reducing oligosaccharide as the main ingredient of the sweetener can be inhibited, resulting in completing a syrupy sweetener with a relatively-high quality and product value. The syrupy sweetener of the present invention can be optionally, advantageously made into a more highly-valued syrupy sweetener by mixing with other saccharide sweeteners and high intensity sweeteners in any step before completion of the final product as long as the objects of the present are not lost.

The syrupy sweetener, which contains a reducing saccharide together with a non-reducing oligosaccharide having a β-fructofuranosidic linkage and whose coloration is inhibited by the present invention, can be stably stored at ambient temperature for a relatively long period of time and it retains its satisfactory taste, and therefore it can be advantageously used intact or incorporated with other sweeteners such as high intensity sweeteners and then injected into containers for use as table sweeteners or portion-type sweeteners. The syrupy sweetener, which contains a reducing saccharide together with a non-reducing oligosaccharide having a β-fructofuranosidic linkage and whose coloration is inhibited by the present invention, can be optionally, advantageously pulverized by appropriate methods, for example, a pulverization method after drying by a drum dryer, and a spray-drying method such as a rotating-disk method, pressure-nozzle method, and two-fluid-nozzle method. It can be advantageously practiced for use in such a manner of making the syrupy sweetener into a non-centrifugal sugar crystal in the form of a paste or solid such as a fondant or icing, or the syrupy sweetener can be used in orally ingestible products including feeds for domestic animals, pet animals, etc in addition to food products for human.

The following experiments explain the present invention in detail.

EXPERIMENT 1

Effects of Various Organic Acid Salts on the Inhibition of Coloration of a Syrupy Sweetener Comprising Lactosucrose and Reducing Saccharides Into "NYUKA OLIGO 700®", a syrupy sweetener comprising lactosucrose (content: about 70 w/w %, d.s.b.) and reducing saccharides (content: 10 w/w % or higher, d.s.b.) such as glucose, fructose, lactose, etc., with a solid concentration of about 75 w/w %, commercialized by Hayashibara Shoji Inc., Okayama, Japan; an aqueous solution containing either of ammonium adipate, sodium citrate, sodium succinate, sodium acetate, sodium potassium tartrate, sodium lactate, calcium lactate, sodium fumarate, or sodium malate in a concentration of 20 mM was incorporated as an organic acid salt to give a final concentration of 1 mM, respectively. Then, the resulting syrups were preserved at 40° C. for 8 weeks as a relatively inclement condition in the preservation at ambient temperatures. Aliquots were sampled from each syrup sample at the points of the start of preservation, 3 weeks after, and 8 weeks after, and then subjected to analyses. At the point of 3 weeks after, samples showing the degree of coloring higher than 0.1 were judged to be not preferable and were excluded from further analyses, and at the point of 8 weeks after, the remaining samples were analyzed. A syrup prepared by adding the same volume of water as the organic acid salt solution as a substitute to the syrupy sweetener was used as the control.

The pH, the content of lactosucrose, and the degree of coloring of the samples were selected as measuring items. The pH was measured using "HM-20E" a pH meter commercialized by To a Denpa KK, Tokyo, Japan, after adjusting the concentration of each syrupy sweetener to Brix 30±1%. The content of lactosucrose as an effective ingredient was determined by HPLC analysis. Analytical conditions of HPLC were as follows:

HPLC column: "TSK GEL AMIDE80" (ID: 4.6 mm, Length: 250 mm), commercialized by Tosoh Corporation, Tokyo, Japan;
Sample volume: 10 µl, adjusted to give a concentration of Brix 3±0.2%;
Column temperature: 35° C.;
Mobile phase: Acetonitrile/Water (71/29);
Flow rate: 1.0 ml/min; and
Detection: Refractive index detector.

The degree of coloring was determined by the steps of measuring the absorbances at 420 nm and 720 nm of each sample adjusted to give a concentration of Brix 30±1% using "UV-2400PC", a spectrophotometer commercialized by Shimadzu Corporation, Kyoto, Japan, and subtracting the absorbance at 720 nm at cell length of 10 cm from that at 420 nm.

The results are in Table 1. In the case of the control, i.e., a sample without any organic acid salt, the degree of coloring was increased and the pH of the syrup was lowered with time. Accompanied with those, the content of lactosucrose as a major component was lowered. Among the samples prepared by adding organic acid salts, in the cases of samples prepared by adding ammonium adipate, sodium citrate, sodium succinate, sodium acetate, sodium potassium tartrate, or sodium fumarate, the degrees of lowering of the pH were small in comparison with that of the control, and the content of lactosucrose were not changed at 3 weeks after from the start of the preservation.

However, since the samples were significantly colored and the degrees of coloring were higher than 0.1, they were judged to be not preferable. In the case of the sample prepared by adding sodium malate, the content of lactosucrose was not changed at 8 weeks after the start of the preservation, however, the degree of coloring was higher than 0.1 and judged to be not preferable.

On the contrary, different from the other sample prepared by adding organic acid salts, in the cases of samples prepared by adding sodium lactate or calcium lactate, the lowering of lactosucrose content and the coloration of the syrupy sweetener were significantly inhibited at 8 weeks after the start of the preservation. Therefore, it was revealed that they can be used for stably preserving the syrupy sweetener with a high quality.

TABLE 1

| | Organic acid salt | | pH | | | Lactosucrose (%) | | | Degree of coloring | | |
|---|---|---|---|---|---|---|---|---|---|---|---|
| | Variety | Final Conc. | At the start of preservation | 3 weeks after | 8 weeks after | At the start of preservation | 3 weeks after | 8 weeks after | At the start of preservation | 3 weeks after | 8 weeks after |
| Control | None | — | 4.51 | 3.95 | 3.53 | 71.2 | 62.3 | 40.7 | 0.045 | 0.068 | 0.080 |
| 1 | Ammonium adipate | 1 mM | 5.91 | 5.69 | — | 71.3 | 71.0 | — | 0.062 | 0.132 | — |

TABLE 1-continued

|  | Organic acid salt | | pH | | | Lactosucrose (%) | | | Degree of coloring | | |
|---|---|---|---|---|---|---|---|---|---|---|---|
|  | Variety | Final Conc. | At the start of preservation | 3 weeks after | 8 weeks after | At the start of preservation | 3 weeks after | 8 weeks after | At the start of preservation | 3 weeks after | 8 weeks after |
| 2 | Sodium citrate | 1 mM | 5.86 | 5.76 | 5.61 | 71.3 | 71.1 | 71.0 | 0.050 | 0.104 | — |
| 3 | Sodium succinate | 1 mM | 5.89 | 5.73 | — | 71.3 | 71.3 | — | 0.074 | 0.120 | — |
| 4 | Sodium acetate | 1 mM | 5.73 | 5.45 | — | 71.4 | 71.4 | — | 0.048 | 0.110 | — |
| 5 | Sodium potassium tartrate | 1 mM | 5.63 | 5.32 | — | 71.2 | 71.3 | — | 0.054 | 0.114 | — |
| 6 | Sodium lactate | 1 mM | 5.38 | 5.17 | 4.98 | 71.2 | 70.9 | 70.8 | 0.050 | 0.062 | 0.065 |
| 7 | Calcium lactate | 1 mM | 5.76 | 5.41 | 5.15 | 71.4 | 70.8 | 70.6 | 0.053 | 0.064 | 0.066 |
| 8 | Sodium fumarate | 1 mM | 6.04 | 5.83 | — | 71.3 | 70.8 | — | 0.077 | 0.139 | — |
| 9 | Sodium malate | 1 mM | 5.96 | 5.69 | 5.46 | 71.5 | 71.2 | 71.5 | 0.064 | 0.071 | 0.139 |

EXPERIMENT 2

Effects of the Concentrations of Sodium Lactate on the Inhibition of Coloration of a Syrupy Sweetener Comprising a Non-Reducing Oligosaccharide Having β-fructofuranosidic Linkage and Reducing Saccharides Into "NYUKA OLIGO 700®", a syrupy sweetener comprising lactosucrose (content: about 70 w/w %, d.s.b.) and reducing saccharides (content: 10 w/w % or higher, d.s.b.) such as glucose, fructose, lactose, etc., with a solid concentration of about 75 w/w %, commercialized by Hayashibara Shoji Inc., Okayama, Japan; an aqueous sodium lactate solution with a concentration of 2, 4, 8, 12, 16, 20, 30, 40, 100, or 200 mM was incorporated to give a final concentration of 0.1, 0.2, 0.4, 0.6, 0.8, 1.0, 1.5, 2.0, 5.0, or 10.0 mM. Then, each sample was preserved at 40° C. for 8 weeks. Aliquots were sampled from each sample at the points of the start of preservation, 4 weeks after, and 8 weeks after, and then subjected to analyses. A syrupy sample prepared by adding the same volume of water as the sodium lactate solution as a substitute to the syrupy sample was used as a control. The pH and the content of lactosucrose of the samples were selected as measuring items and measured according to the same conditions as in Experiment 1. Further, at 8 weeks after, the degree of coloring of each sample was also measured.

The results are in Table 2. In the case of the control, i.e., a sample without sodium lactate, the pH of the sample was lowered with time, and accompanied with this, the content of lactosucrose as a major component was lowered. Also in the case of the sample with a final sodium lactate concentration of 0.1 mM, similar results to those of the control were obtained.

In the cases of samples with final sodium lactate concentrations of 0.2 mM or higher, it was revealed that the lowering of lactosucrose is inhibited.

However, in the cases of the sample with the concentration of higher than 2.0 mM, it was revealed that the degree of coloring of the sample was higher than 0.1 and the sample is judged to be not preferable. From the above results, it was revealed that, in the cases of samples with a sodium lactate concentration of 0.2 mM or higher but 2.0 mM or lower, preferably, 0.2 mM or higher but 1.5 mM or lower, the coloration of the syrupy sweetener and the content reduction of lactosucrose are inhibited.

TABLE 2

|  | Concentration of sodium lactate (mM) | pH | | | Lactosucrose (%) | | | Degree of coloring | |
|---|---|---|---|---|---|---|---|---|---|
|  |  | At the start of preservation | 4 weeks after | 8 weeks after | At the start of preservation | 4 weeks after | 8 weeks after | At the start of preservation | 8 weeks after |
| Control | 0 | 4.91 | 4.00 | 3.79 | 71.7 | 61.9 | 44.2 | 0.046 | 0.081 |
| 1 | 0.1 | 5.00 | 4.27 | 3.97 | 71.7 | 68.8 | 59.7 | 0.049 | 0.067 |
| 2 | 0.2 | 5.09 | 4.71 | 4.39 | 71.7 | 70.7 | 70.1 | 0.047 | 0.050 |
| 3 | 0.4 | 5.25 | 4.90 | 4.73 | 71.4 | 71.0 | 70.6 | 0.051 | 0.051 |
| 4 | 0.6 | 5.33 | 4.97 | 4.84 | 71.6 | 71.1 | 71.4 | 0.045 | 0.055 |
| 5 | 0.8 | 5.42 | 5.06 | 4.93 | 71.3 | 71.5 | 70.9 | 0.049 | 0.058 |
| 6 | 1.0 | 5.48 | 5.11 | 5.01 | 71.5 | 71.0 | 71.1 | 0.048 | 0.065 |
| 7 | 1.5 | 5.65 | 5.23 | 5.17 | 71.2 | 71.1 | 71.0 | 0.052 | 0.065 |
| 8 | 2.0 | 6.38 | 5.37 | 5.15 | 71.1 | 71.3 | 71.5 | 0.050 | 0.073 |
| 9 | 5.0 | 6.58 | 5.57 | 5.38 | 71.9 | 72.2 | 71.9 | 0.051 | 0.092 |
| 10 | 10.0 | 6.73 | 5.74 | 5.52 | 71.2 | 72.2 | 71.9 | 0.052 | 0.110 |

EXPERIMENT 3

Effects of the Concentrations of Sodium Lactate on the Taste of a Syrupy Sweetener Comprising a Non-Reducing Oligosaccharide Having a β-Fructofuranosidic Linkage and Reducing Saccharides Into "NYUKA OLIGO 700®", a syrupy sweetener comprising lactosucrose (content: about 70 w/w %, d.s.b.) and reducing saccharides (content: 10 w/w % or higher, d.s.b.) such as glucose, fructose, lactose, etc., with a solid concentration of about 75 w/w %, commercialized by Hayashibara Shoji Inc., Okayama, Japan, sodium lactate was incorporated to give a final concentration of 0.1, 0.2, 0.5, 1.0, 1.5, 2.0, 5.0, or 10.0 mM, and then, the resulting samples were subjected to tasting whether the taste of each sample was different from that of a syrupy sweetener without sodium lactate or not. A sensory evaluation was carried out by 14 panelists, and the differences of taste between samples with various sodium lactate concentrations and the control were judged by the following 3 levels, i.e., "Significant", "Slight", and "None".

The results are in Table 3. The tastes of syrupy sweeteners, prepared by adding sodium lactate to give a final concentration of 0.1 to 1.5 mM, were not different from that of a control, i.e., a syrupy sweetener without sodium lactate. In the case of the syrupy sweetener with a sodium lactate concentration of 2.0 mM, 12 in 14 panelists did not feel any difference in taste and only 2 panelists felt a slight difference, and they judged that the tastes of the samples were slightly different in comparison with that of the control. On the contrary, in the cases of the syrupy sweeteners with sodium lactate with concentrations of 5.0 and 10 mM, 6 and 13 in 14 panelists felt difference in taste, respectively, and it was revealed that the syrupy sweeteners are not preferable. From the above results, it was revealed that, in the cases of the sodium lactate concentrations of lower than 2.0 mM, desirably, lower than 1.5 mM, the taste of the syrupy sweetener is not deteriorated.

TABLE 3

| Concentration of sodium lactate | Difference in taste from that of control | | |
|---|---|---|---|
| | Significant | Slight | None |
| 0.1 mM | 0 | 0 | 14 |
| 0.2 mM | 0 | 0 | 14 |
| 0.5 mM | 0 | 0 | 14 |
| 1.0 mM | 0 | 0 | 14 |
| 1.5 mM | 0 | 0 | 14 |
| 2.0 mM | 0 | 2 | 12 |
| 5.0 mM | 4 | 2 | 8 |
| 10.0 mM | 8 | 5 | 1 |

EXPERIMENT 4

Effects of Various Organic Acid Salts on the Inhibition of Coloration of a Syrupy Sweetener Comprising Glycosylsucrose and Reducing Saccharides Into "COUPLING SUGAR®", a syrupy sweetener comprising glycosylsucroses (content: about 55 w/w %, d.s.b.) and reducing saccharides (content: 10 w/w % or higher, d.s.b.) such as glucose, maltooligosaccharides, fructose, etc., with a solid concentration of about 75 w/w %, commercialized by Hayashibara Shoji Inc., Okayama, Japan, an aqueous solution containing either of sodium citrate, sodium succinate, sodium lactate, and calcium lactate in a concentration of 20 mM was incorporated as an organic acid salt to give a final concentration of 1 mM, respectively, and the resulting syrups were preserved at 40° C. for 4 weeks. Aliquots were sampled from each syrupy sample at the points of the start of preservation, 2 weeks after, and 4 weeks after, and then subjected to analyses. A syrup, prepared by adding the same volume of water as the organic acid salt solution as a substitute to the syrupy sweetener, was used as a control. According to the methods in Experiment 1, the pH, the content of glucosylsucrose (or erlose) which is one of glycosylsucroses, and the degree of coloring were measured.

The results are in Table 4. In the case of the control, i.e., a sample without any organic acid salt, the pH of the syrup was lowered with time and accompanied with this, the content of glucosylsucrose as a major component in the syrup was also lowered. On the contrary, in any case of samples prepared by adding organic acid salts, it was revealed that the lowering of pH was inhibited and glucosylsucrose can be preserved stably because the content of glucosylsucrose was not changed from that at the start of the preservation. However, it was revealed that samples prepared by adding sodium citrate or sodium succinate are not preferable because the degree of coloring after 4 weeks preservation was 0.1 or higher, revealing that the coloration of the syrupy sweetener was accelerated. It was also revealed that, in the cases of samples prepared by adding sodium lactate or calcium lactate, the coloration of the syrupy sweetener and the content reduction of glucosylsucrose were inhibited.

TABLE 4

| | | | pH | | | Glucosylsucrose (%) | | | Degree of coloring | | |
|---|---|---|---|---|---|---|---|---|---|---|---|
| | Organic acid salt | | At the start of preservation | 2 weeks after | 4 weeks after | At the start of preservation | 2 weeks after | 4 weeks after | At the start of preservation | 2 weeks after | 4 weeks after |
| | Variety | Final Conc. | | | | | | | | | |
| Control | None | — | 4.36 | 3.89 | 3.58 | 23.2 | 21.8 | 17.9 | 0.019 | 0.025 | 0.031 |
| 1 | Sodium citrate | 1 mM | 6.43 | 6.09 | 5.84 | 23.2 | 23.5 | 22.9 | 0.033 | 0.096 | 0.133 |
| 2 | Sodium succinate | 1 mM | 6.18 | 5.89 | 5.63 | 23.2 | 23.6 | 23.3 | 0.034 | 0.089 | 0.118 |
| 3 | Sodium lactate | 1 mM | 5.34 | 5.15 | 5.01 | 23.3 | 23.4 | 23.0 | 0.024 | 0.035 | 0.042 |
| 4 | Calcium lactate | 1 mM | 5.80 | 5.44 | 5.26 | 23.3 | 23.4 | 23.3 | 0.030 | 0.045 | 0.046 |

The following examples further explain the present invention in detail. However, the present invention is not restricted by them.

EXAMPLE 1

Syrupy Sweetener Comprising Lactosucrose and Reducing Saccharides

An aqueous solution containing sucrose at a concentration of 22 w/w % of and lactose at a concentration of 18 w/w %, was adjusted to pH 6.0. The resultant solution was admixed with β-fructofuranosidase in an amount of 1 unit per one gram of sucrose and an invertase-deficient yeast in an amount of five percentage of wet weight of the yeast per dry weight of the saccharides, and allowed to react at 35° C. for 20 hours with keeping the pH in a range of 6 to 7 with 1 N sodium hydroxide solution. After heated at 90° C. for 30 minutes to inactivate the enzyme, the solution was cooled and purified by decoloring and filtering with an activated charcoal and desalting with ion-exchange resins in H- and OH-form in conventional manner. Further, the resultant solution was concentrated to obtain a syrupy sweetener (solid concentration of 75 w/w %) comprising lactosucrose (content of about 70 w/w %, d.s.b.) and reducing saccharides (content of 10 w/w % or more, d.s.b.) such as glucose, fructose and lactose. Into 100 parts by weight of the syrupy sweetener, one part by weight of 40 mM sodium lactate was incorporated, and the resultant mixture was homogeneously blended. Since the product contains sodium lactate at a concentration of 0.4 mM, the product is a high-quality syrupy sweetener comprising lactosucrose and reducing saccharides whose coloration is inhibited when stored at ambient temperature.

EXAMPLE 2

Syrupy Sweetener Comprising Lactosucrose and Reducing Saccharides

A solution, containing sucrose and lactose at a concentration of 20 w/w %, respectively, was adjusted to pH 5.5, admixed with β-fructofuranosidase in an amount of one unit per one gram of sucrose, and allowed to react at 50° C. for 16 hours. After heated at 90° C. for 30 minutes to inactivate the enzyme, the solution was cooled and purified by decoloring and filtering with an activated charcoal and desalting with ion-exchange resins in H and OH-form in conventional manner. Further the resultant solution was concentrated to obtain a syrupy sweetener (dry solid concentration of 75 w/w %) comprising lactosucrose (content of about 45 w/w %, d.s.b.) and reducing saccharides (content of 10 w/w % or more, d.s.b.) such as glucose, fructose and lactose. The syrupy sweetener was admixed with a hydrous calcium lactate powder to give a concentration of 0.3 mM. The product is a high-quality syrupy sweetener comprising lactosucrose and reducing saccharides whose coloration is inhibited in storage at ambient temperature.

EXAMPLE 3

Syrupy Sweetener Comprising Glycosylsucrose and Reducing Saccharides

Milky solution of cornstarch at a concentration of 33 w/w % was adjusted to pH 6.5, admixed with "TERMAMYL 60L" (an α-amylase product produced by Novozymes) in an amount of 0.2 w/w % per one gram of starch, and allowed to react at 95° C. to give DE value of 5.0. After the reaction was terminated by autoclave (120° C., 10 minutes), the resultant reaction solution was cooled, admixed with sucrose in an amount of 20 w/w % and cyclomaltodextrin glucanotransferase in an amount of three units per one gram of starch, and allowed to react at pH 5.6 and 65° C. for 24 hours. After heated at 95° C. for 30 minutes to inactivate the enzyme, the reaction solution was cooled and purified by decoloring and filtering with an activated charcoal and desalting with ion-exchange resins in H- and OH-form in conventional manner. Further the resultant solution was concentrated to obtain a syrupy sweetener (dry solid concentration of 75 w/w %) comprising glycosylsucrose (content of about 55 w/w %, d.s.b.) and reducing saccharides (content of 10 w/w % or more, d.s.b.) such as glucose, maltooligosaccharides and fructose. Into 100 parts by weight of the syrupy sweetener, five parts by weight of 10 mM sodium lactate solution was incorporated, and the resultant mixture was homogeneously blended. Since the product contains sodium lactate at a concentration of about 0.5 mM, the product is a high-quality syrupy sweetener comprising glycosylsucrose and reducing saccharides whose coloration is inhibited when stored at ambient temperature.

EXAMPLE 4

Syrupy Sweetener Comprising Fructooligosaccharides and Reducing Sacchardes

Into 100 parts by weight of "MEIOLIGO G" (a syrupy sweetener comprising fructooligosaccharides (content of about 55 w/w %, d.s.b.) and reducing saccharides (content of about 30 w/w % or more, d.s.b.) such as glucose and fructose, dry solid concentration of 75 w/w %, commercialized by Meiji Seika Kaisha, Ltd.), five parts by weight of 10 mM sodium lactate solution was incorporated, and the resultant mixture was homogeneously blended. Since the product comprises sodium lactate at a concentration of about 0.5 mM, the product is a high-quality syrupy sweetener comprising fructooligosaccharides and reducing saccharides whose coloration is inhibited when stored at ambient temperature.

EXAMPLE 5

Table Sweetener

The syrupy sweetener whose coloration was inhibited, produced by the method of Example 2, was poured into a plastic container with a capacity of 300 ml to obtain a table sweetener. Since the product contains calcium lactate at a concentration of about 0.3 mM, the product is a high-quality syrupy sweetener whose coloration was inhibited when stored at ambient temperature.

EXAMPLE 6

Table Sweetener

Into 100 parts by weight of the syrupy sweetener whose coloration was inhibited, produced by the method of Example 1, five parts by weight of sucralose (produced by San-Ei Gen F. F. I., Inc.) was homogeneously mixed to give about twice the degree of sweetness of sucrose, on a dry solid basis. The resultant sweetener was poured into a plastic bottle with a capacity of 500 ml to obtain a table sweetener. Since the product contains sodium lactate at a concentration of about 0.4 mM, the product was a high-quality syrupy sweetener having preferable taste whose coloration is inhibited when stored at ambient temperature. Also, since the product has the same sweetness as the half amount of sucrose, the product can be advantageously used for sweetening low-calorie foods and drinks.

EXAMPLE 7

Sweetener for Coffee and Tea

Five grams of the syrupy sweetener whose coloration was inhibited, produced by the method of Example 1, was poured into a small plastic container to obtain a portion-size sweetener. Since the product contains sodium lactate at a concentration of about 0.4 mM, the product is a high-quality syrupy sweetener for beverage whose coloration is inhibited when stored at ambient temperature and can be used for a sweetener for coffee and tea.

EXAMPLE 8

Coffee Lightener

A mixture of 108 parts by weight of an unsalted butter and 342 parts by weight of a hydrogenated rapeseed oil (melting point of 25 to 28° C.) was heated at 70 to 75° C., admixed with 7.2 parts by weight of soy lecithin and 4.5 parts by weight of sucrose fatty acid ester (HBL value of 1) and dissolved to prepare an oil phase. A water phase was prepared by dissolving 57.6 parts by weight of skim milk, 81 parts by weight of casein sodium, 63 parts by weight of trehalose, 20 parts by weight of the syrupy sweetener whose coloration was inhibited, produced by the method of Example 1, 2.7 parts by weight of polyglycerol fatty acid ester (HBL value of 14), 3.6 parts by weight of sucrose fatty acid ester (HBL value of 15), 3.6 parts by weight of dibasic potassium phosphate and 5.4 parts by weight of dibasic sodium phosphate in 1,103.4 parts by weight of water at a temperature of 70 to 75° C. The water phase and the oil phase were put into a homogenizer, pre-emulsified with heating at 70 to 75° C. for 15 minutes with stirring, and homogenized under two-step pressure (180 kg/cm$^2$ in the first step, 50 kg/cm$^2$ in the second step). After the resultant emulsion was put into a UTH sterilizer and sterilized by heating at 145° C. for two seconds, the emulsion was further homogenized aseptically with heating at 70° C. under two-step pressure (100 kg/cm$^2$ in the first step, 50 kg/cm$^2$ in the second step) and dispensed in an amount of 5 ml per a polystyrene container, and the container was sealed to obtain a coffee lightener. The product is a coffee lightener having preferable taste usable as a lightener or sweetener for coffee and tea.

EXAMPLE 9

Yoghurt Beverage

A mixture of 100 parts by weight of yoghurt, 70 parts by weight of the syrupy sweetener whose coloration was inhibited, produced by the method of Example 1, 30 parts by weight of the syrupy sweetener whose coloration was inhibited, produced by the method of Example 3, 10 parts by weight of trehalose, 0.25 part by weight of yoghurt flavor, and 0.1 part by weight of lemon extract, was filled up to 1,000 parts by weight with water to obtain a yoghurt beverage.

Since the product comprises lactosucrose and glycosylsucrose, it is a yoghurt beverage having preferable taste.

EXAMPLE 10

Custard Cream

A sufficiently mixed mixture of 100 parts by weight of corn starch, 100 parts by weight of the syrupy sweetener whose coloration was inhibited, produced by the method of Example 1, 80 parts by weight of maltose, 20 parts by weight of sucrose, and one part by weight of salt was admixed with 280 parts by weight of hen egg, stirred, admixed with 1,000 parts by weight of boiled milk little by little. The mixture continued stirring over a fire until translucent by complete gelatinization of the cornstarch. After the mixture was cooled, it was admixed with an adequate amount of vanilla flavor, weighed, poured into a container, and packaged to give a final product. The product is a custard cream having smooth gloss and preferable taste.

EXAMPLE 11

Fondant

A mixture of 154 parts by weight of "TREHA®" (α,α-trehalose commercialized by Hayashibara Biochemical Laboratories, Inc.), 40 parts by weight of the syrupy sweetener whose coloration was inhibited, produced by the method of Example 3, and 25 parts by weight of water was boiled down until the concentration increased up to 77 w/w %, cooled down to 70° C., and stirred to obtain a fondant. The product is a fondant having good color and glaze and preferable taste.

EXAMPLE 12

Jelly

A mixture of 10 parts by weight of the syrupy sweetener whose coloration was inhibited, produced by the method of Example 1, 2.5 parts by weight of gelatin, 35 parts by weight of commercial orange juice, five parts by weight of lemon juice, 47.5 parts by weight of water and 0.05 part by weight of sucralose was kept at 80° C. for 25 minutes, dispended into cups, cooled down to room temperature and further cooled in a refrigerator to obtain a jelly. The product is a jelly having preferable taste.

EXAMPLE 13

Bean Jam

Ten parts by weight of raw red bean was boiled in water, and rid of astringency, harshness and water-soluble trash in conventional manner to prepare about 21 parts by weight of a red bean jam containing bean skins. After the resultant plain bean jam was admixed with 14 parts by weight of sucrose, five parts by weight of the syrupy sweetener whose coloration was inhibited, produced by the method of Example 2, and four parts by weight of water, the bean jam mixture was boiled, admixed with a small amount of salad oil, and kneaded without breaking the bean skins to obtain about 35 parts by weight of a bean jam product.

The product is a bean jam having preferable taste and can be used as a material for sweets such as a bean-jam bread, bean-jam bun, rice dumpling, wafer cake, and ice milk.

EXAMPLE 14

Powdery Sweetener Comprising Lactosucrose

The syrupy sweetener whose coloration was inhibited, produced by the method of Example 1, was heated up to 50° C. and spray-dried to obtain a powdery sweetener comprising lactosucrose. The product is a high-quality sweetener having preferable taste comprising lactosucrose and reducing saccharides.

EXAMPLE 15

"Uiro-no-moto" (Instant "Uiro")

Ninety parts by weight of rice flour, 20 parts by weight of corn starch, 40 parts by weight of sucrose, 80 parts by weight of the powdery sweetener comprising lactosucrose and reducing saccharides produced by the method of Example 14, and four parts by weight of pullulan were homogeneously blended to obtain "Uiro-no-moto". A mixture of the above "uiro-no-moto", adequate amounts of green powdered tea and water was kneaded, poured into a container and steamed for 60 minutes to obtain a green tea "uiro". The product is a "uiro" having good gloss and preferable taste.

EXAMPLE 16

Hard Candy

A mixture of 95 parts by weight of a reduced maltose syrup (dry solid concentration of about 75 w/w %) and 15 parts by weight of the syrupy sweetener whose coloration was inhibited, produced by the method of Example 1, was prepared with heating, concentrated until the water content decreased to less than 2 w/w % under a reduced pressure. The resultant mixture was admixed with one part by weight of citric acid, and adequate amounts of lemon juice and coloring agent, and molded in conventional manner to obtain a hard candy. The product is an anticarious hard candy having preferable taste.

EXAMPLE 17

Hard Candy

A mixture of 60 parts by weight of sucrose, 40 parts by weight of an enzymatically saccharified syrup (dry solid concentration of about 75 w/w %) and 10 parts by weight of the syrupy sweetener whose coloration was inhibited, produced by the method of Example 3, was dissolved in 15 parts by weight of water with heating, and the mixture was concentrated until the water content decreased to less than 3 w/w % under a reduced pressure. The mixture was admixed with one part by weight of citric acid, and adequate amounts of lemon juice and coloring agent, and molded in conventional manner to obtain a hard candy.

The product is an anticarious hard candy having preferable taste.

EXAMPLE 18

Feed Composition

Forty parts by weight of powdery dried gluten, 38 parts by weight of skim milk, 15 parts by weight of the syrupy sweetener whose coloration was inhibited, produced by the method of Example 2, 10 parts by weight of vitamin preparation, five parts by weight of fish powder, five parts by weight of dibasic calcium phosphate, three parts by weight of liquid fat, three parts by weight of calcium carbonate, two parts by weight of salt, and two parts by weight of mineral preparation were blended to obtain a feed composition. The product is a feed composition preferable for domestic animals and fowls, especially for piglets. The product can be made into other form of feed composition by incorporating other feed materials such as thick feed materials including cereal, wheat flour, starch, oilcake and bran, and crude feed materials including straw, hay, bagasse, and corncob.

INDUSTRIAL APPLICABILITY

As explained above, in the present invention, the coloration of a syrupy sweetener comprising a reducing saccharide together with a non-reducing oligosaccharide having a β-fructofuranosidic linkage is inhibited by incorporating a lactate thereinto, and also the content reduction of the oligosaccharide having a β-fructofuranosidic linkage as major ingredient is inhibited thereby. Also, a syrupy sweetener comprising a reducing saccharide together with a non-reducing oligosaccharide having β-fructofuranosidic linkage, which is stable when stored at ambient temperature, can be produced thereby.

The present invention, which has established a method for inhibiting coloration of a syrupy sweetener comprising a reducing saccharide together with a non-reducing oligosaccharide having a β-fructofuranosidic linkage without deteriorating the taste inherent to the syrupy sweetener, and is applicable for food products and materials such as table sweetener having good keeping quality, has a great significance in the field of food industry.

The invention claimed is:

1. A method for inhibiting, the coloring of a lactosucrose syrup, which comprises a step of incorporating a lactate into said lactosucrose syrup which comprises lactosucrose and one or more reducing saccharides selected from the group consisting glucose, fructose, and lactose and has a solid concentration in the range of 30 to 80 w/w %, to give a lactate concentration in the range of 0.2 to 2 mM, whereby the coloring of said lactosucrose syrup is inhibited.

2. The method of claim 1, wherein said lactate is sodium lactate.

* * * * *